United States Patent
Kubo et al.

(10) Patent No.: US 7,932,502 B2
(45) Date of Patent: Apr. 26, 2011

(54) FLUORESCENCE OBSERVATION APPARATUS

(75) Inventors: Kei Kubo, Hino (JP); Shunji Takei, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 12/834,331

(22) Filed: Jul. 12, 2010

(65) Prior Publication Data

US 2011/0017923 A1    Jan. 27, 2011

Related U.S. Application Data

(63) Continuation of application No. PCT/JP2009/067667, filed on Oct. 9, 2009.

(30) Foreign Application Priority Data

Mar. 30, 2009 (JP) ................................ 2009-083210

(51) Int. Cl.
G01J 1/58 (2006.01)
(52) U.S. Cl. .................................. 250/458.1; 250/459.1
(58) Field of Classification Search ............... 250/458.1, 250/459.1
See application file for complete search history.

(56) References Cited

U.S. PATENT DOCUMENTS

| | | | |
|---|---|---|---|
| 5,003,977 A | 4/1991 | Suzuki et al. | |
| 2004/0245350 A1 | 12/2004 | Zeng | |
| 2006/0247535 A1 | 11/2006 | Sendai | |
| 2006/0262211 A1* | 11/2006 | Kido ............................ | 348/308 |
| 2008/0015446 A1* | 1/2008 | Mahmood et al. ............ | 600/476 |
| 2008/0039697 A1 | 2/2008 | Morishita | |

FOREIGN PATENT DOCUMENTS

| | | |
|---|---|---|
| JP | 01-250740 | 10/1989 |
| JP | EP 1 705 477 A2 | 9/2006 |
| JP | 2006-263044 | 10/2006 |
| JP | 2006-526767 | 11/2006 |
| JP | 2008-043396 | 2/2008 |
| JP | 2008-148791 | 7/2008 |
| JP | 2008-161550 | 7/2008 |
| WO | WO 2004/106896 A2 | 12/2004 |

OTHER PUBLICATIONS

International Search Report dated Dec. 15, 2009.

* cited by examiner

*Primary Examiner* — David P Porta
*Assistant Examiner* — Mark R Gaworecki
(74) *Attorney, Agent, or Firm* — Scully, Scott, Murphy & Presser, P.C.

(57) ABSTRACT

A fluorescence observation apparatus according to the present invention includes a light source section that emits excitation light for exciting a first fluorescent substance and a second fluorescent substance, a fluorescence detection section that detects first fluorescent light emitted when the first fluorescent substance is excited and second fluorescent light emitted when the second fluorescent substance is excited, a correction value calculation section that calculates a correction value for canceling a color mixture between the first fluorescent light and the second fluorescent light based on feature values corresponding to characteristics of the first fluorescent substance and the second fluorescent substance, a detected image generation section that generates a first detected image corresponding to a detection result of the first fluorescent light and a second detected image corresponding to a detection result of the second fluorescent light, and an image correction section that corrects a luminance value of the first detected image to a luminance value corresponding to intensity of the first fluorescent light and corrects a luminance value of the second detected image to a luminance value corresponding to intensity of the second fluorescent light.

9 Claims, 7 Drawing Sheets

FLUORESCENCE OBSERVATION APPARATUS

CROSS REFERENCE TO RELATED APPLICATION

This application is a continuation application of PCT/JP2009/067667 filed on Oct. 9, 2009 and claims benefit of Japanese Application No. 2009-083210 filed in Japan on Mar. 30, 2009, the entire contents of which are incorporated herein by this reference.

BACKGROUND OF THE INVENTION

1. Field of the Invention

The present invention relates to a fluorescence observation apparatus, and more particularly, to a fluorescence observation apparatus for observing fluorescent light beams emitted from a plurality of fluorescent substances.

2. Description of the Related Art

Cancer diagnosis techniques using molecular targeting agents are becoming a focus of attention in recent years. To be more specific, for example, a technique of scattering or injecting a fluorescent probe (fluorescence agent) targeting at biological protein that is developed specifically in cancer cells and then identifying the presence/absence of cancer based on fluorescent light emitted from the target region is under study in recent years. Such a technique is useful for early detection of cancer in the field of the digestive tract.

Furthermore, as an application of the aforementioned technique, a technique is being proposed which is designed to scatter or inject a plurality of types of fluorescent probes into a target region of a living body and observe the developed state of a plurality of types of biological protein corresponding to the plurality of types of fluorescent probes in a composite manner based on fluorescent light of a plurality of wavelengths emitted from the target region. Such a technique is considered useful for estimation of stages of cancer, prediction of risk of cancer invasion and prediction of risk of cancer metastasis or the like.

For example, Japanese Patent Application Laid-Open Publication No. 2008-161550 and Japanese Patent Application Laid-Open Publication No. 2008-148791 disclose an endoscope system that makes observations by scattering or injecting a plurality of types of fluorescent probes into a target region of a living body, configured to be able to acquire a fluorescence image (image of a fluorescent light distribution) for each fluorescent probe by carrying out calculation processing based on a relationship between the intensity of fluorescent light and concentration of the fluorescent probe obtained during the observations.

SUMMARY OF THE INVENTION

A fluorescence observation apparatus according to the present invention includes a light source section that emits excitation light for exciting a first fluorescent substance and a second fluorescent substance, a fluorescence detection section that detects first fluorescent light emitted when the first fluorescent substance is excited by the excitation light and second fluorescent light emitted when the second fluorescent substance is excited by the excitation light, a correction value calculation section that calculates a correction value for canceling a color mixture between the first fluorescent light and the second fluorescent light based on feature values corresponding to characteristics of the first fluorescent substance and the second fluorescent substance, a detected image generation section that generates a first detected image corresponding to a detection result of the first fluorescent light in the fluorescence detection section and a second detected image corresponding to a detection result of the second fluorescent light in the fluorescence detection section, and an image correction section that corrects a luminance value of each pixel of the first detected image to a luminance value corresponding to intensity of the first fluorescent light and corrects a luminance value of each pixel of the second detected image to a luminance value corresponding to intensity of the second fluorescent light based on the correction value.

A fluorescence observation apparatus according to the present invention includes a light source section that emits excitation light to an object to be examined having a first fluorescent substance and a second fluorescent substance, a fluorescence detection section that detects first fluorescent light emitted when the first fluorescent substance is excited by the excitation light and second fluorescent light emitted when the second fluorescent substance is excited by the excitation light, a correction value calculation section that calculates a correction value based on a first spectral image obtained by picking up an image of the object to be examined formed by light of a wavelength band that excites the first fluorescent substance and a second spectral image obtained by picking up an image of the object to be examined formed by light of a wavelength band that excites the second fluorescent substance, a detected image generation section that generates a first detected image corresponding to a detection result of the first fluorescent light in the fluorescence detection section and a second detected image corresponding to a detection result of the second fluorescent light in the fluorescence detection section, and an image correction section that corrects a luminance value of each pixel of the first detected image to a luminance value corresponding to intensity of the first fluorescent light and corrects a luminance value of each pixel of the second detected image to a luminance value corresponding to intensity of the second fluorescent light based on the correction values.

DETAILED DESCRIPTION OF THE PREFERRED EMBODIMENTS

Hereinafter, embodiments of the present invention will be described with reference to the accompanying drawings.

First Embodiment

FIG. 1 to FIG. 8 are related to a first embodiment of the present invention.

Figure 1:
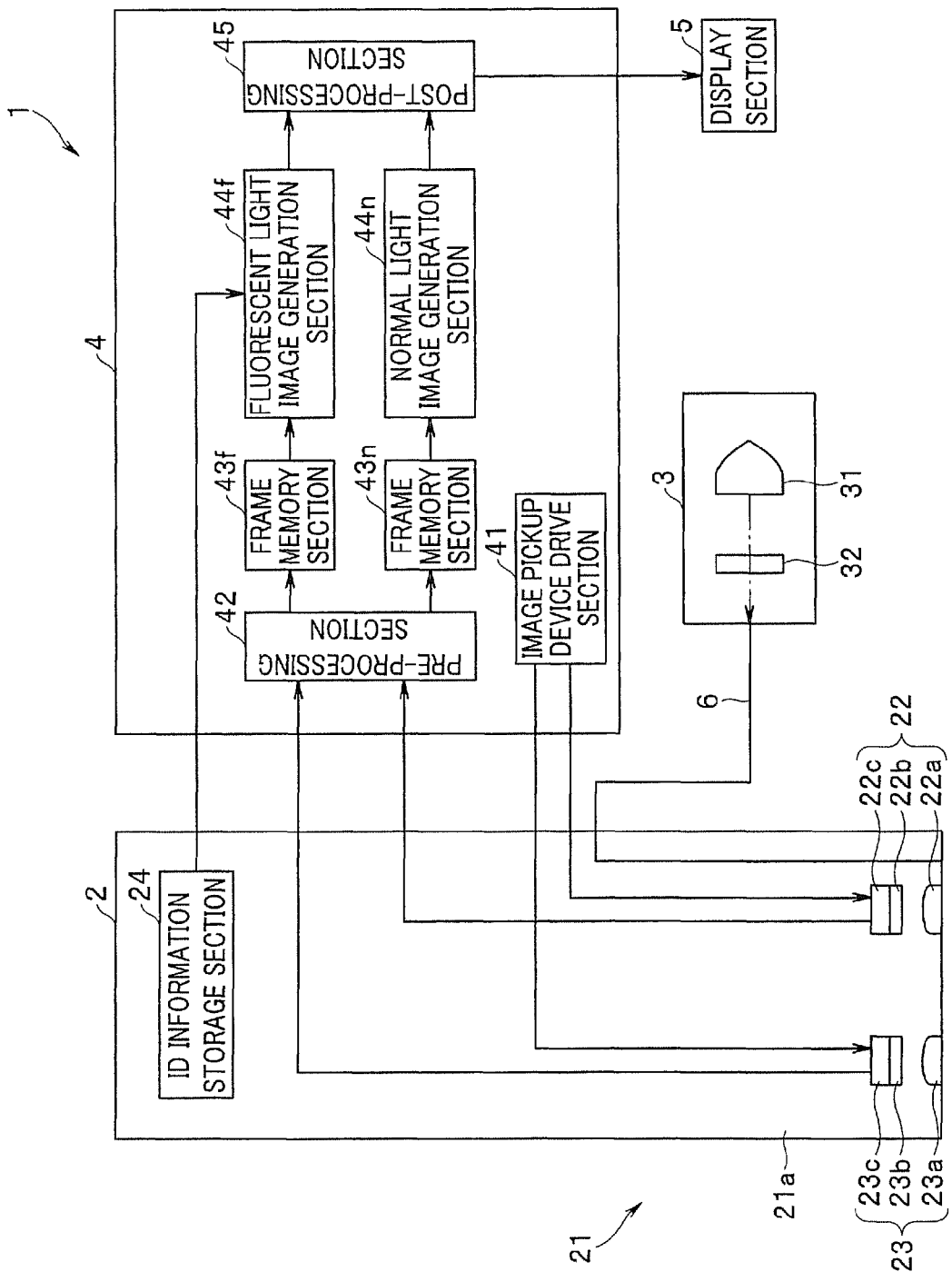
FIG. 1 is a diagram illustrating a configuration of main parts of an endoscope system according to a first embodiment of the present invention.

As shown in FIG. 1, an endoscope system 1 as a fluorescence observation apparatus includes an endoscope 2 that acquires an object image in the body cavity of an examinee and outputs an image pickup signal according to the object image, a light source apparatus 3 that supplies illumination light to be emitted to the object to the endoscope 2, a processor 4 that converts the image pickup signal outputted from the endoscope 2 to a video signal and outputs the video signal and a display section 5 that displays an object image according to the video signal outputted from the processor 4.

The endoscope 2 includes a long flexible insertion portion 21. Furthermore, a light guide 6 for transmitting illumination light emitted from the light source apparatus 3 to a distal end portion 21a is inserted in the insertion portion 21.

One end face (incidence end face) of the light guide 6 is connected to the light source apparatus 3. Furthermore, the other end face (exit end face) of the light guide 6 is disposed in the vicinity of an illumination optical system (not shown) provided at the distal end portion 21a. With such a configuration, illumination light emitted from the light source apparatus 3 is emitted to an object through the light guide 6 and the illumination optical system (not shown).

The distal end portion 21a of the insertion portion 21 is provided with a normal light image pickup system 22 and a fluorescent light image pickup system 23.

The normal light image pickup system 22 is configured by including an objective optical system 22a that forms an object image, a color filter 22b disposed after the objective optical system 22a and an image pickup device 22c disposed after the color filter 22b and at an image forming position of the objective optical system 22a.

The color filter 22b is configured as one in which an R filter that allows to pass a red color region (excluding regions from a near-infrared region onward), a G filter that allows to pass a green color region and a B filter that allows to pass a blue color region out of returning light that has passed through the objective optical system 22a are arranged in a matrix form.

The image pickup device 22c is driven according to the control of the processor 4 and converts an object image corresponding to the light that has passed through the color filter 22b to an image pickup signal and outputs the image pickup signal.

The fluorescent light image pickup system 23 provided with the function as a fluorescence detection section is configured by including an objective optical system 23a that forms an object image, a fluorescence detection filter 23b disposed after the objective optical system 23a and an image pickup device 23c disposed after the fluorescence detection filter 23b and at an image forming position of the objective optical system 23a.

Figures 2, 3:
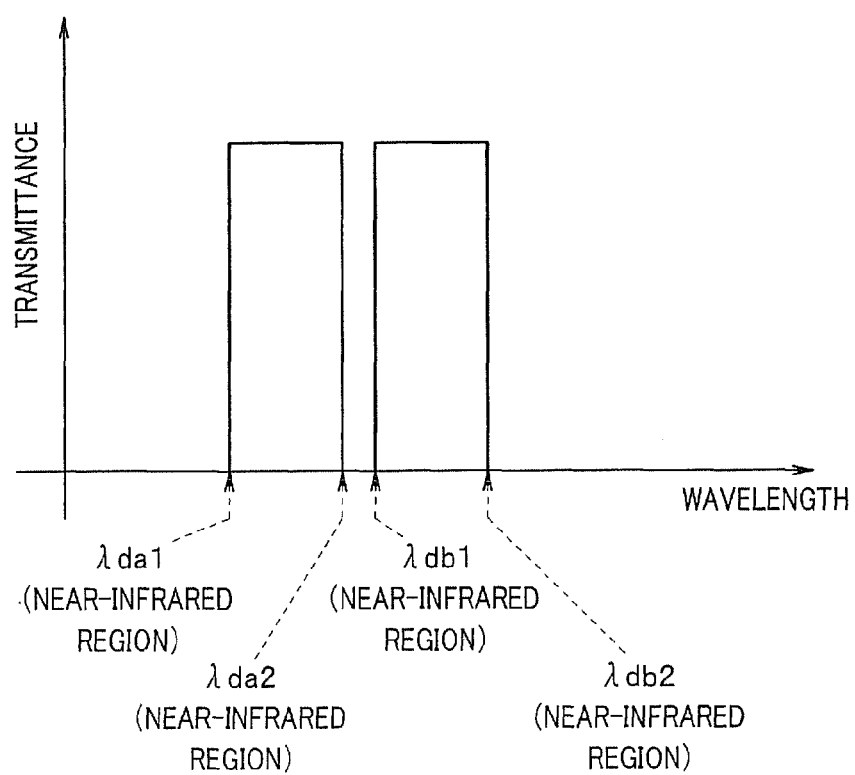
FIG. 2 is a diagram illustrating an example of configuration of a fluorescence detection filter provided for the endoscope in FIG. 1.
FIG. 3 is a diagram illustrating an example of transmission characteristics of the fluorescence detection filter in FIG. 2.

As shown in FIG. 2, the fluorescence detection filter 23b is configured as one in which filters 231 that allow to pass a wavelength band of fluorescent light emitted from a first fluorescent probe and filters 232 that allow to pass a wavelength band of fluorescent light emitted from a second fluorescent probe out of the returning light that has passed through the objective optical system 23a are arranged in a matrix form. (In FIG. 2, locations of the filters 231 are shown by D1 and locations of the filters 232 are shown by D2.)

Hereinafter, a case will be described assuming that, for example, ICG (indocyanine green) and Cy7 (registered trademark) are used together, that is, when all the excitation wavelength of the first fluorescent probe and maximum fluorescent light wavelength, and the excitation wavelength of the second fluorescent probe and maximum fluorescent light wavelength exist in the near-infrared region.

To be more specific, the filter 231 is configured to allow to pass the first detected wavelength band of wavelength $\lambda da1$ to $\lambda da2$ of the near-infrared region including the wavelength band of the fluorescent light emitted from the first fluorescent probe as shown in FIG. 3. On the other hand, the filter 232 is configured to allow to pass the second detected wavelength band of wavelength $\lambda db1$ to $\lambda db2$ of the near-infrared region which is the wavelength band that includes the wavelength band of the fluorescent light emitted from the second fluorescent probe as shown in FIG. 3 and does not overlap with the first detected wavelength band.

The transmittances of the color filter 22b, the filter 231 and the filter 232 may be adjusted beforehand so that the brightness of the returning light received at the image pickup device 22c and the brightness of the fluorescent light emitted from the first and (or) the second fluorescent probe and then received at the image pickup device 23c are optimally balanced (so that those luminance values fall within the dynamic range of each image pickup device). Furthermore, the transmittances of the filter 231 and the filter 232 may be adjusted beforehand so that the brightness of the fluorescent light emitted from the first fluorescent probe and received by the image pickup device 23c and the brightness of the fluorescent light emitted from the second fluorescent probe and received by the image pickup device 23c are optimally balanced (so that those luminance values fall within the dynamic range of the image pickup device 23c).

The image pickup device 23c is made up of a high sensitivity CCD or the like capable of detecting fluorescent light emitted from the first and second fluorescent probes. Furthermore, the image pickup device 23c is driven according to the control of the processor 4, converts an object image corresponding to the light that has passed through the fluorescence detection filter 23b to an image pickup signal and outputs the image pickup signal.

On the other hand, an ID information storage section 24 that stores at least information on the wavelength band passed through the filters 231 and 232 is provided in the endoscope 2. The information is outputted to the processor 4 when the endoscope 2 and the processor 4 are electrically connected.

The light source apparatus 3 as a light source section is configured by including a lamp 31 and a filter 32 disposed on the optical path of the lamp 31.

The lamp 31 is made up of a xenon lamp or the like capable of emitting white color light including at least a band from the blue color region to the near-infrared region.

Furthermore, a diaphragm (not shown) for adjusting the light quantity of white color light emitted from the lamp 31 is disposed between the lamp 31 and the filter 32. The aforementioned diaphragm may be adjusted to an appropriate amount of diaphragm based on the brightness of a normal light image outputted from a normal light image generation section 44n of the processor 4 or to an amount of diaphragm according to the user's operation.

Figure 4:
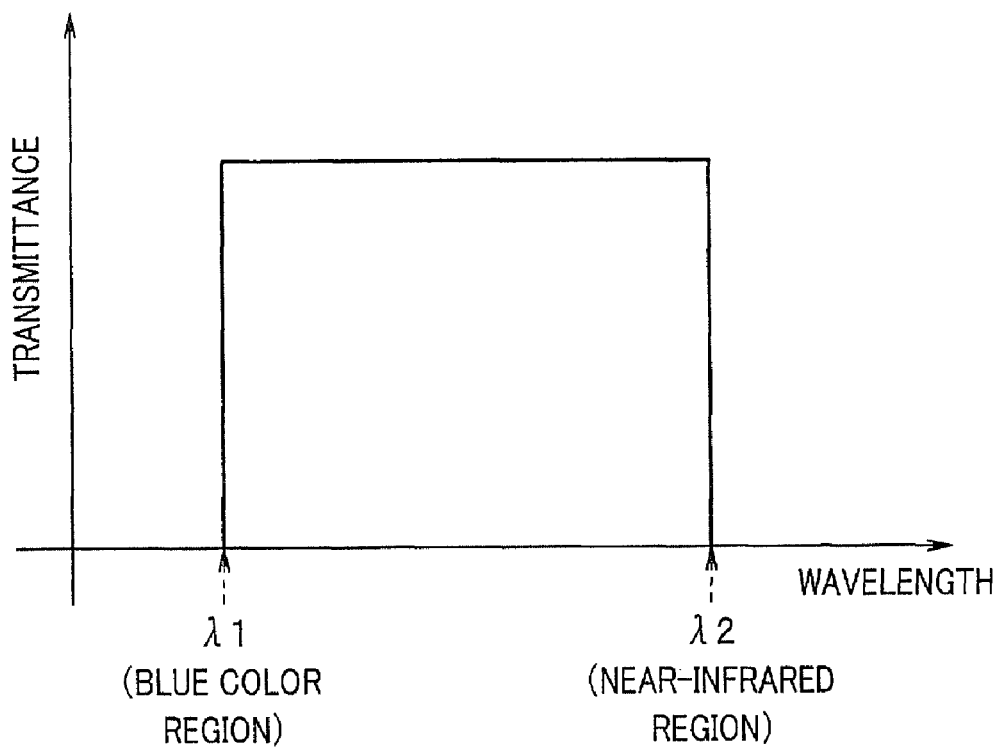
FIG. 4 is a diagram illustrating an example of transmission characteristics of the filter provided for the light source apparatus in FIG. 1.

The filter 32 is configured to allow to pass a band from a wavelength λ1 of the blue color region to a wavelength λ2 of the near-infrared region out of the white color light emitted from the lamp 31 as shown in FIG. 4.

The processor 4 is configured by including an image pickup device drive section 41, a pre-processing section 42, frame memory sections 43n and 43f, the normal light image generation section 44n, a fluorescent light image generation section 44f and a post-processing section 45.

The image pickup device drive section 41 performs control so as to drive the image pickup devices 22c and 23c while causing output timings of their image pickup signals to match.

The pre-processing section 42 applies signal processing such as amplification, noise reduction and A/D conversion to the first image pickup signal outputted from the image pickup device 22c and outputs the first image pickup signal after the signal processing to the frame memory section 43n. Furthermore, the pre-processing section 42 applies signal processing such as amplification, noise reduction and A/D conversion to the second image pickup signal outputted from the image pickup device 23c and outputs the second image pickup signal after the signal processing to the frame memory section 43f.

The frame memory section 43n stores the first image pickup signal outputted from the pre-processing section 42 in units of one frame. On the other hand, the frame memory section 43f stores the second image pickup signal outputted from the pre-processing section 42 in units of one frame.

The normal light image generation section 44n reads the latest one-frame portion of the first image pickup signal stored in the frame memory section 43n, generates a normal light image (full color image) corresponding to the image pickup signal and outputs the normal light image to the post-processing section 45.

Figure 5:
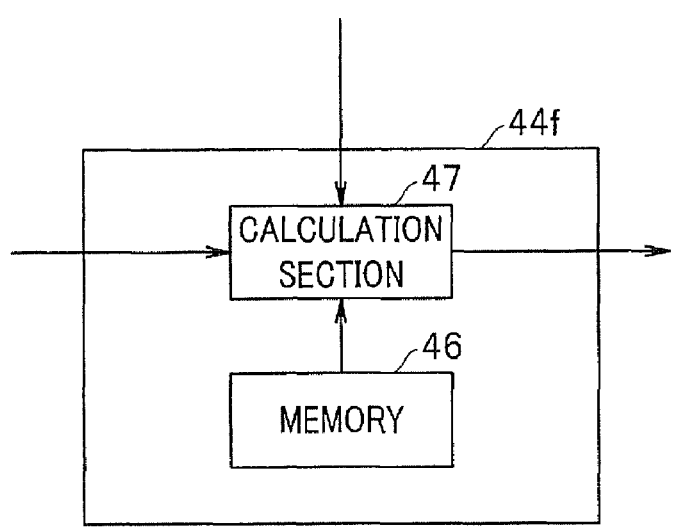
FIG. 5 is a diagram illustrating an example of configuration of the fluorescent light image generation section in FIG. 1.

As shown in FIG. 5, the fluorescent light image generation section 44f is configured by including a memory 46 that stores fluorescence spectral waveforms of a plurality of fluorescent probes and a calculation section 47.

The calculation section 47 reads information on wavelength bands passed through the filters 231 and 232 from the ID information storage section 24 when the endoscope 2 and the processor 4 are electrically connected and further reads a fluorescence spectral waveform of the fluorescent probe corresponding to the information from the memory 46. Furthermore, the calculation section 47 provided with the function as a correction value calculation section performs predetermined calculation processing based on the information read from the ID information storage section 24 and the fluorescence spectral waveform read from the memory 46, thereby calculates correction values $\alpha$ and $\beta$ to be used to generate a fluorescent light image and then temporarily stores the calculation results of the correction values $\alpha$ and $\beta$ in the memory 46.

On the other hand, the calculation section 47 provided with the function as a detected image generation section reads the latest one-frame portion of the second image pickup signal stored in the frame memory section 43f, performs predetermined image processing thereon and thereby generates a first fluorescence detected image corresponding to the detection result of the fluorescent light emitted from the first fluorescent probe and a second fluorescence detected image corresponding to the detection result of the fluorescent light emitted from the second fluorescent probe.

After that, based on the calculation results of the correction values $\alpha$ and $\beta$ and the first and second fluorescence detected images, the calculation section 47 provided with the function as an image correction section generates a first fluorescent light image provided with a luminance value corresponding to the intensity of the fluorescent light emitted from the first fluorescent probe and a second fluorescent light image provided with a luminance value corresponding to the intensity of the fluorescent light emitted from the second fluorescent probe and outputs the images to the post-processing section 45.

The details of the method of generating the first and second fluorescent light images including the aforementioned predetermined calculation processing and predetermined image processing will be described later.

The post-processing section 45 applies processing such as D/A conversion to the normal light image outputted from the normal light image generation section 44n and the first and second fluorescent light images outputted from the fluorescent light image generation section 44f and then outputs those images to the display section 5 as video signals.

Next, the operation of the endoscope system 1 will be described.

First, after connecting each section of the endoscope system 1, the user turns on power to the each section. Accordingly, the calculation section 47 detects that the endoscope 2 and the processor 4 are electrically connected and reads feature values corresponding to characteristics of the first and second fluorescent probes from the memory 46 respectively. To be more specific, upon detecting that the endoscope 2 and the processor 4 are electrically connected, the calculation section 47 reads the information on the wavelength bands transmitted from the filters 231 and 232 from the ID information storage section 24 and further reads the fluorescence spectral waveforms of the fluorescent probes corresponding to the information from the memory 46.

Figure 6:
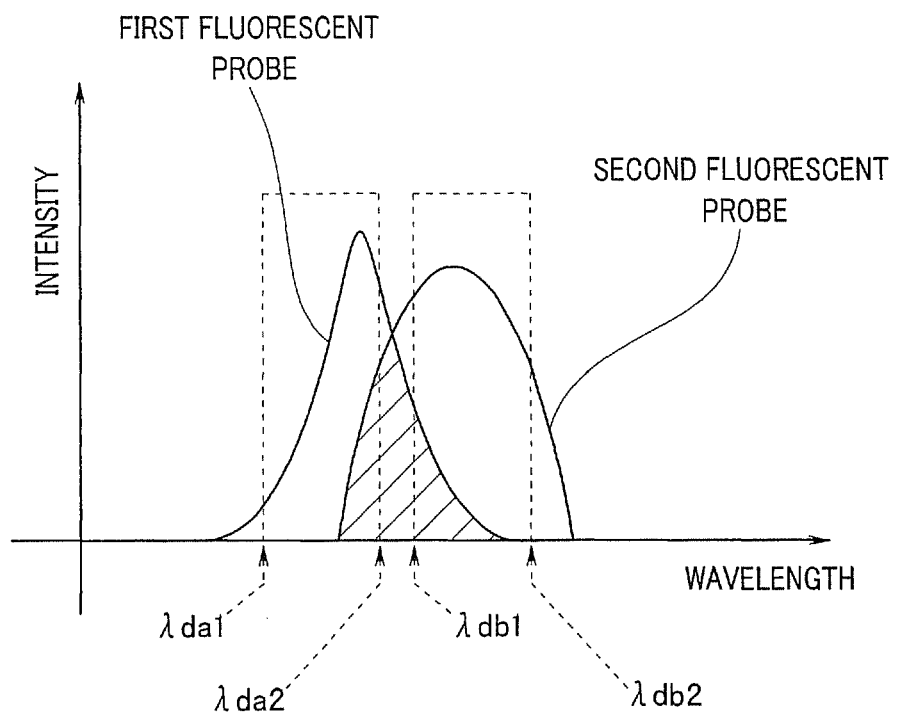
FIG. 6 is a diagram illustrating a relationship between a spectral waveform of fluorescent light emitted from each fluorescent probe and each detected wavelength band.

Here, a case will be described as a specific example where the fluorescence spectral waveforms of the first and second fluorescent probes overlap with each other in the diagonally shaded area in FIG. 6 and the fluorescence spectral waveforms of the first and second fluorescent probes, the first detected wavelength band (wavelength $\lambda da1$ to $\lambda da2$) passed through the filter 231 and the second detected wavelength band (wavelength $\lambda db1$ to $\lambda db2$) passed through the filter 232 have a relationship as shown in FIG. 6.

Figure 7:
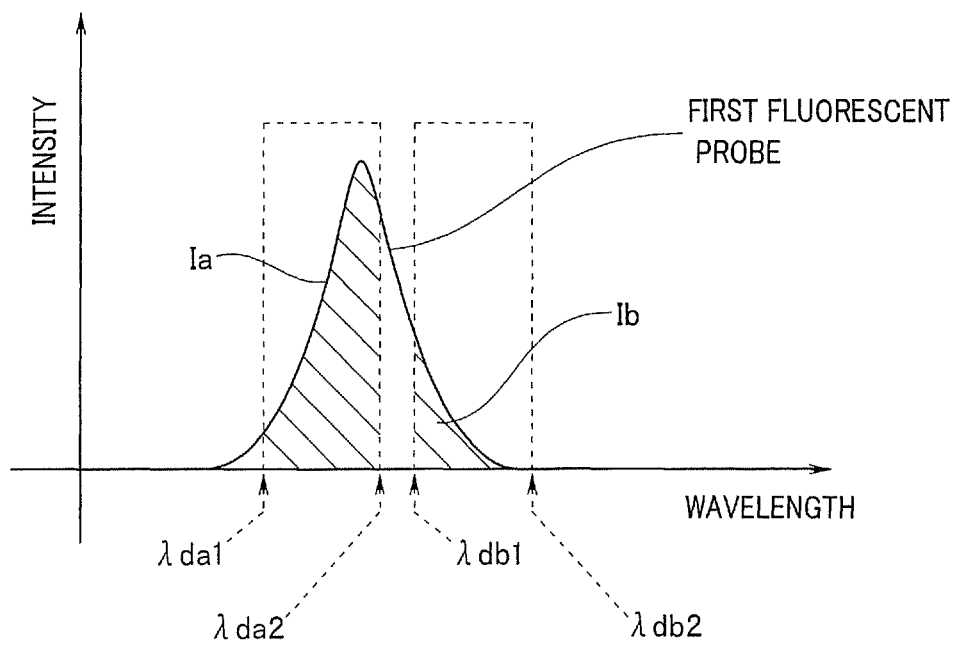
FIG. 7 is a diagram illustrating a portion where a spectral waveform of fluorescent light emitted from the first fluorescent probe and each detected wavelength band overlap with each other.

The calculation section 47 integrates a first function corresponding to the fluorescence spectral waveform of the first fluorescent probe in the range from the wavelength $\lambda da1$ to $\lambda da2$, and thereby calculates an integral value Ia of the region enclosed by the fluorescence spectral waveform of the first fluorescent probe and the first detected wavelength band (see FIG. 7). Furthermore, the calculation section 47 integrates the first function in the range from the wavelength $\lambda db1$ to $\lambda db2$, and thereby calculates an integral value Ib of the region enclosed by the fluorescence spectral waveform of the first fluorescent probe and the second detected wavelength band (see FIG. 7). Furthermore, the calculation section 47 subtracts the value of the integral value Ia from the value of the integral value Ib, and thereby calculates the aforementioned correction value $\beta$.

Figure 8:
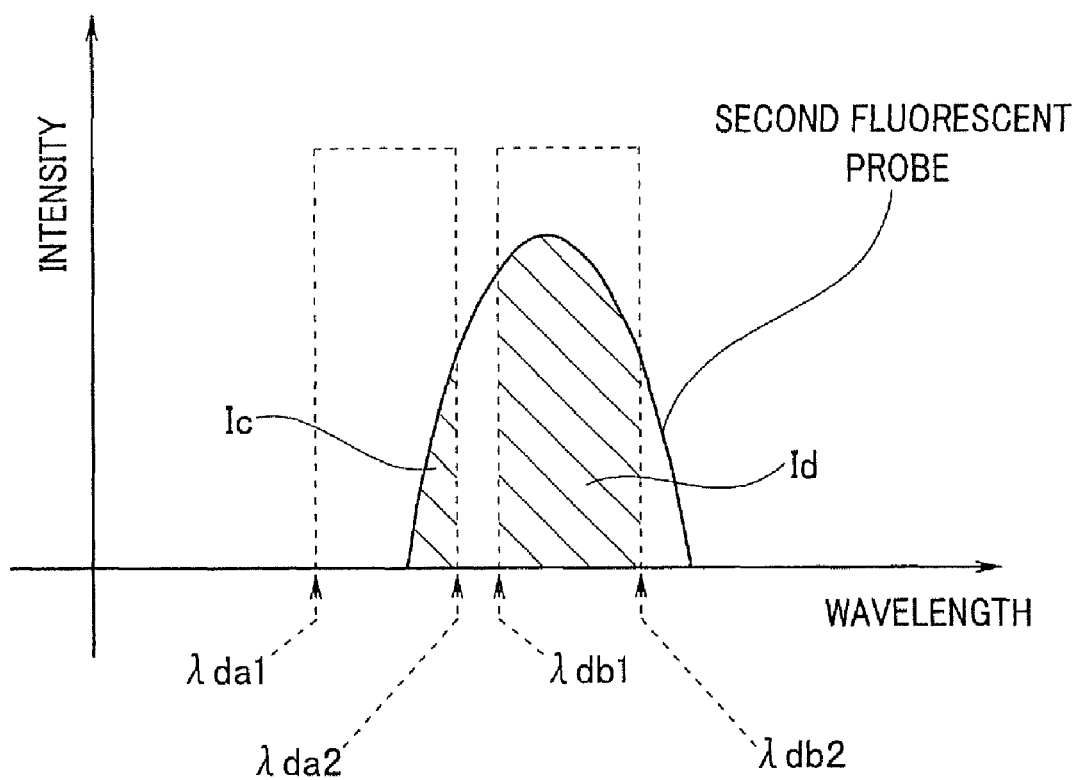
FIG. 8 is a diagram illustrating a portion where a spectral waveform of fluorescent light emitted from the second fluorescent probe and each detected wavelength band overlap with each other.

The calculation section 47 integrates a second function corresponding to the fluorescence spectral waveform of the second fluorescent probe in the range from the wavelength $\lambda da1$ to $\lambda da2$, and thereby calculates an integral value Ic of the region enclosed by the fluorescence spectral waveform of the second fluorescent probe and the first detected wavelength band (see FIG. 8). Furthermore, the calculation section 47 integrates the second function in the range from the wavelength λdb1 to λdb2, and thereby calculates an integral value Id of the region enclosed by the fluorescence spectral waveform of the second fluorescent probe and the second detected wavelength band (see FIG. 8). The calculation section 47 then subtracts the value of the integral value Id from the value of the integral value Ic, and thereby calculates the aforementioned correction value α.

When the filters 231 and 232 having preadjusted transmittances are used, an adjusted transmittance ta of the filter 231 and an adjusted transmittance tb of the filter 232 may be stored in the ID information storage section 24 beforehand and the following calculation may be carried out so as to calculate the correction values α and β.

To be more specific, before and after calculating the aforementioned each integral value, the calculation section 47 reads the adjusted transmittance ta of the filter 231 and the adjusted transmittance tb of the filter 232 from the ID information storage section 24. The calculation section 47 then subtracts the value resulting from multiplying the integral value Ia by the transmittance ta from the value resulting from multiplying the integral value Ib by the transmittance tb, and thereby calculates the aforementioned correction value β. Furthermore, the calculation section 47 subtracts the value resulting from multiplying the integral value Id by the transmittance tb from the value resulting from multiplying the integral value Ic by the transmittance ta, and thereby calculates the aforementioned correction value α.

After that, the calculation section 47 temporarily stores the calculation results of the correction values α and β obtained by the aforementioned calculation processing in the memory 46.

However, when the fluorescence spectral waveforms of the first and second fluorescent probes do not overlap with each other and the diagonally shaded area in FIG. 6 does not exist, both the integral values Ib and Ic are 0. In such a case, the calculation section 47 temporarily stores α=0 and β=0 as the calculation results of the correction values in the memory 46.

The fluorescent light image generation section 44f is not limited to the one that calculates each integral value of the Ia, Ib, Ic and Id using the fluorescence spectral waveforms stored in the memory 46 beforehand and may also be one that stores table data in which fluorescent light intensities of a plurality of fluorescent probes are described in units of wavelength 1 nm and calculates a value corresponding to the each integral value using the table data. In such a case, the calculation section 47 performs the following processing.

When the endoscope 2 and the processor 4 are electrically connected, the calculation section 47 reads information on the wavelength bands transmitted from the filters 231 and 232 from the ID information storage section 24 and further reads the table data of the fluorescent probes corresponding to the information from the memory 46.

The calculation section 47 calculates the sum of fluorescence intensities of the first fluorescent probe at wavelength λda1 to λda2 with reference to the table data read from the memory 46, and thereby acquires the value corresponding to the aforementioned integral value Ia.

Furthermore, the calculation section 47 calculates the sum of fluorescence intensities of the first fluorescent probe at wavelength λdb1 to λdb2 with reference to the table data read from the memory 46, and thereby acquires the value corresponding to the aforementioned integral value Ib.

Furthermore, the calculation section 47 calculates the sum of fluorescence intensities of the second fluorescent probe at wavelength λda1 to λda2 with reference to the table data read from the memory 46, and thereby acquires the value corresponding to the aforementioned integral value Ic.

Furthermore, the calculation section 47 calculates the sum of fluorescence intensities of the second fluorescent probe at wavelength λdb1 to λdb2 with reference to the table data read from the memory 46, and thereby acquires the value corresponding to the aforementioned integral value Id.

According to the above-described calculation processing using the table data related to the fluorescence intensities of the fluorescent probes, it is possible to reduce the load of the calculation section 47 compared to the calculation processing using fluorescence spectral waveforms of the fluorescent probes.

On the other hand, the user inserts the insertion portion 21 of the endoscope 2 into the body cavity of the examinee and installs the distal end portion 21a so that illumination light is emitted to the position where a desired object such as cancer exists.

The user then scatters or injects the first and second fluorescent probes into the desired object such as cancer, using a treatment instrument (not shown) having a shape and size that allows it to be inserted into the endoscope 2.

When the first and second fluorescent probes are scattered or injected into the desired object such as cancer, first fluorescent light having intensity corresponding to the amount of first biological protein which is the target of the first fluorescent probe and second fluorescent light having intensity corresponding to the amount of second biological protein which is the target of the second fluorescent probe are emitted simultaneously. Returning light having the first fluorescent light and the second fluorescent light is impinged on the objective optical systems 22a and 23a respectively.

The returning light impinged on the objective optical system 22a passes through the color filter 22b and becomes RGB light composed of light of a red color region corresponding to the transmission band of the R filter, light of a green color region corresponding to the transmission band of the G filter and light of a blue color region corresponding to the transmission band of the B filter. The image pickup device 22c converts the object image corresponding to the RGB light to an image pickup signal and then outputs the image pickup signal to the processor 4.

On the other hand, the returning light impinged on the objective optical system 23a passes through the fluorescence detection filter 23b and becomes color mixed light composed of light of the first detected wavelength band corresponding to the transmission band of the filter 231 (first fluorescent light) and light of the second detected wavelength band corresponding to the transmission band of the filter 232 (second fluorescent light). The image pickup device 23c then converts the object image corresponding to the color mixture light to an image pickup signal and outputs the image pickup signal to the processor 4.

The first image pickup signal outputted from the image pickup device 22c is subjected to the aforementioned signal processing by the pre-processing section 42, stored in the frame memory section 43n and the latest one-frame portion thereof is read by the normal light image generation section 44n. The normal light image generation section 44n then generates a normal light image (full color image) corresponding to the image pickup signal using the latest one-frame portion of the first image pickup signal stored in the frame memory section 43n and outputs the normal light image to the post-processing section 45.

On the other hand, the second image pickup signal outputted from the image pickup device 23c is subjected to the aforementioned signal processing by the pre-processing section 42, stored in the frame memory section 43f and read by the calculation section 47 of the fluorescent light image generation section 44f.

The calculation section 47 generates a first fluorescence detected image corresponding to the detection result of the first fluorescent light using the latest one-frame portion of the second image pickup signal stored in the frame memory section 43f. To be more specific, the calculation section 47 generates the aforementioned first fluorescence detected image by assuming, for example, the luminance value of α pixel corresponding to the location of the filter 232 of the fluorescence detection filter 23b to be an average of luminance values of four pixels in the vicinity of the pixel in the latest one-frame portion of the second image pickup signal stored in the frame memory section 43f.

Furthermore, the calculation section 47 generates a second fluorescence detected image corresponding to the detection result of the second fluorescent light using the latest one-frame portion of the second image pickup signal stored in the frame memory section 43f. To be more specific, the calculation section 47 generates the aforementioned second fluorescence detected image by assuming, for example, the luminance value of α pixel corresponding to the location of the filter 231 of the fluorescence detection filter 23b to be an average of luminance values of four pixels in the vicinity of the pixel in the latest one-frame portion of the second image pickup signal stored in the frame memory section 43f.

Here, the aforementioned correction value β is a value for correcting the luminance value in a band (second detected wavelength band) of the first fluorescent light where a crosstalk phenomenon occurs due to a color mixture with the second fluorescent light. Furthermore, the aforementioned correction value α is a value for correcting the luminance value in a band (first detected wavelength band) of the second fluorescent light where a crosstalk phenomenon occurs due to a color mixture with the first fluorescent light. That is, the aforementioned correction values α and β correspond to correction values to cancel the color mixture of the first fluorescent light and the second fluorescent light.

Here, assuming that the luminance values corresponding to the same pixel in the first and second fluorescence detected images are P1 and P2, the luminance value of the first fluorescent light image corresponding to the intensity of the first fluorescent light is Pa and the luminance value of the second fluorescent light image corresponding to the intensity of the second fluorescent light is Pb, a relationship shown in following equations (1) and (2) holds between the respective values and the correction values α and β.

$$P1 = Pa + \alpha Pb \quad (1)$$

$$P2 = \beta Pa + Pb \quad (2)$$

The calculation section 47 reads the calculation results of the correction values α and β from the memory 46 and then calculates luminance values Pa and Pb for all pixels of the first and second fluorescence detected images using above equations (1) and (2).

Furthermore, the calculation section 47 performs processing of replacing the luminance value P1 by the luminance value Pa for all pixels of the first fluorescence detected image, and thereby generates the aforementioned first fluorescent light image. The first fluorescent light image generated through such processing has only the luminance value corresponding to the intensity of the fluorescent light emitted from the first fluorescent probe, and therefore becomes an image where degradation of contrast caused by a crosstalk phenomenon is drastically reduced.

Furthermore, the calculation section 47 performs processing of replacing the luminance value P2 by the luminance value Pb for all pixels of the second fluorescence detected image, and thereby generates the aforementioned second fluorescent light image. The second fluorescent light image generated through such processing has only the luminance value corresponding to the intensity of the fluorescent light emitted from the second fluorescent probe, and therefore becomes an image where degradation of contrast caused by a crosstalk phenomenon is drastically reduced.

After that, the calculation section 47 outputs the first and second fluorescent light images to the post-processing section 45.

The post-processing section 45 applies processing such as D/A conversion to the normal light image outputted from the normal light image generation section 44n and the first and second fluorescent light images outputted from the fluorescent light image generation section 44f, and then outputs the images to the display section 5 as video signals.

When generating video signals, the post-processing section 45 may perform processing of simultaneously displaying the normal light image, the first fluorescent light image and the second fluorescent light image on one screen or processing of displaying only images corresponding to an instruction given by a display mode changeover switch (not shown).

Furthermore, when generating video signals, the post-processing section 45 may perform processing of displaying any one of the first fluorescent light image and the second fluorescent light image superimposed on the normal light image.

Furthermore, when generating video signals, the post-processing section 45 may perform processing of coloring the first fluorescent light image and the second fluorescent light image in different colors and displaying the colored fluorescent light images superimposed on the normal light image.

As described above, by applying correction processing based on fluorescence spectral waveforms specific to each fluorescent probe to the detection results of a plurality of fluorescent light beams emitted from the plurality of fluorescent probes, the endoscope system 1 has a configuration and operation capable of acquiring a fluorescent light image where degradation of contrast caused by a crosstalk phenomenon is drastically reduced. That is, the endoscope system 1 can stably reduce a crosstalk phenomenon generated when observing fluorescent light emitted from a plurality of fluorescent probes without depending on the concentration of each fluorescent probe, intensity of excitation light and an observation environment such as observation distance.

The present embodiment is not only applicable to a case where two types of fluorescent probes are used together, but also applicable to cases where three or more types of fluorescent probes are used together substantially in the same way.

Second Embodiment

Figure 9:
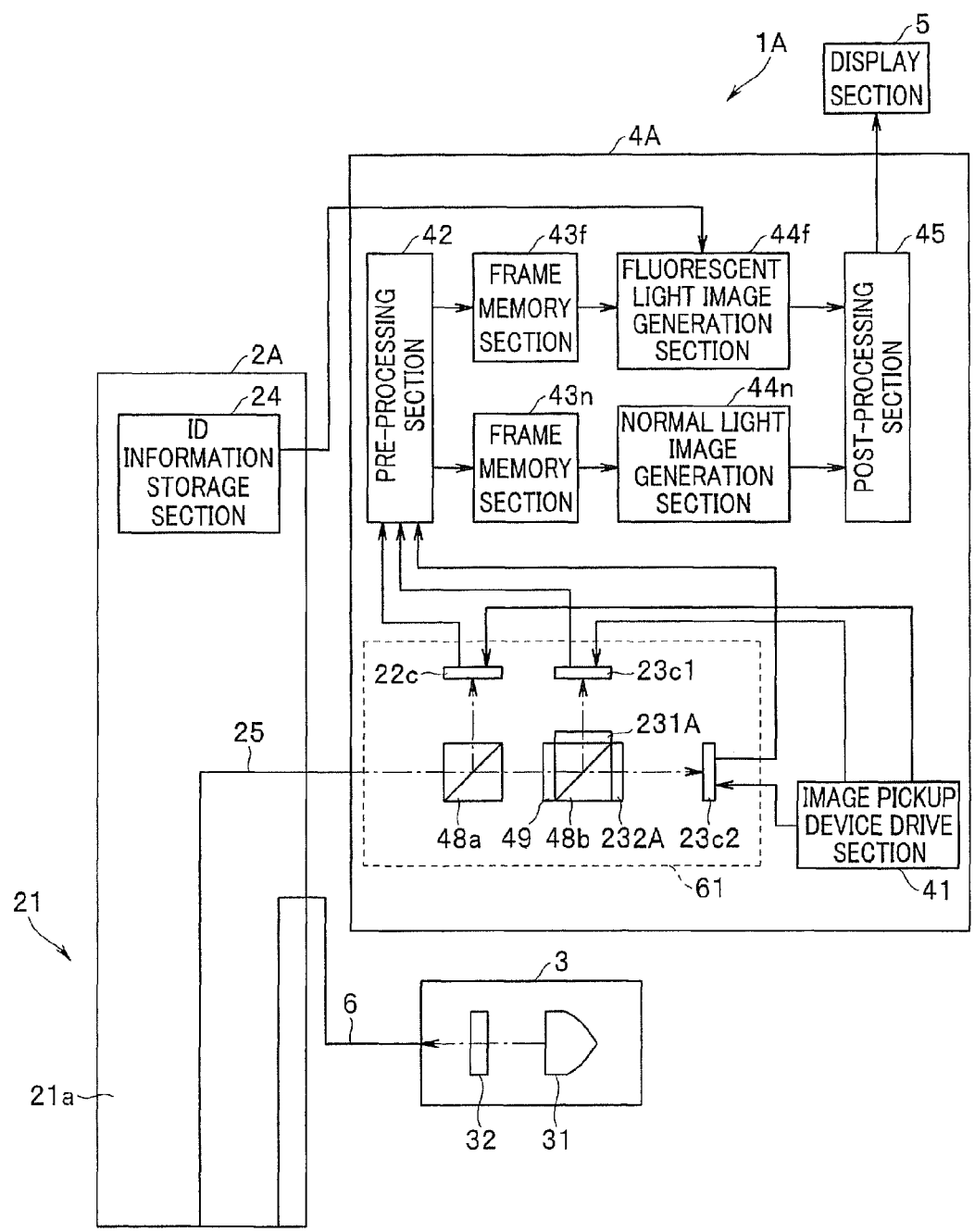
FIG. 9 is a diagram illustrating a configuration of main parts of an endoscope system according to a second embodiment of the present invention.

FIG. 9 is related to a second embodiment of the present invention.

In the following descriptions, detailed descriptions of components similar to those in the first embodiment will be omitted. Furthermore, the configuration of the endoscope system of the present embodiment has a configuration similar to that in the first embodiment. Thus, suppose parts different from those in the first embodiment will be mainly described in the present embodiment.

As shown in FIG. 9, the endoscope system 1A has an endoscope 2A that acquires an optical image of an object in the body cavity of an examinee, a light source apparatus 3 that supplies illumination light to be emitted to the object to the endoscope 2A, a processor 4A that converts the optical image obtained by the endoscope 2A to a video signal and outputs the video signal and a display section 5 that displays an object image corresponding to the video signal outputted from the processor 4A.

The endoscope 2A is configured by removing the normal light image pickup system 22 and the fluorescent light image pickup system 23 from the endoscope 2 of the first embodiment and including an image guide 25 that transmits an optical image of an object in an insertion portion 21.

One end face (incidence end face) of the image guide 25 is disposed in the vicinity of an observation window (not shown) provided in a distal end portion 21a. Furthermore, the other end face (exit end face) of the image guide 25 is connected to the processor 4A. With such a configuration, the optical image of the object acquired in the endoscope 2 is outputted to the processor 4A via the observation window (not shown) and the image guide 25.

The processor 4A is configured by including an image pickup device drive section 41, a pre-processing section 42, frame memory sections 43n and 43f, a normal light image generation section 44n, a fluorescent light image generation section 44f, a post-processing section 45 and an image pickup section 61.

The image pickup section 61 provided with the function as a fluorescence detection section is configured by including an image pickup device 22c, image pickup devices 23c1 and 23c2, dichroic mirrors 48a and 48b, an excitation light cut filter 49, and fluorescence detection filters 231A and 232A.

That is, the image pickup device drive section 41 of the processor 4A performs control of driving the image pickup devices 22c, 23c1 and 23c2 provided in the image pickup section 61 while causing output timings of image pickup signals to match.

The image pickup devices 23c1 and 23c2 are the same as the image pickup device 23c of the first embodiment and disposed on the light reflection side and on the light transmitting side of the dichroic mirror 48b respectively.

An optical image outputted from the other end face (exit end face) of the image guide 25 is impinged on the dichroic mirror 48a. Of the optical images outputted from the other end face (exit end face) of the image guide 25, an RGB image composed of an image of a red color region (excluding regions from the near-infrared region onward), an image of a green color region and an image of a blue color region is reflected toward the image pickup device 22c side and a color mixture image other than the RGB image is passed to the dichroic mirror 48b side. Furthermore, the image pickup device 22c converts the RGB image reflected by the dichroic mirror 48a to an image pickup signal and outputs the image pickup signal to the pre-processing section 42.

On the other hand, the excitation light cut filter 49 is disposed on the optical path that connects the dichroic mirrors 48a and 48b. Thus, the color mixture image that has passed through the dichroic mirror 48a impinges on the dichroic mirror 48b with the wavelength band of excitation light cut by the excitation light cut filter 49.

A part of the color mixture image impinged on the dichroic mirror 48b is reflected toward the fluorescence detection filter 231A side and the other part thereof is passed to the fluorescence detection filter 232A side.

The fluorescence detection filter 231A has characteristics of allowing to pass only light of the first detected wavelength band, that is, is configured to have the same function as the filter 231 of the first embodiment. Furthermore, the fluorescence detection filter 232A has characteristics of allowing to pass only light of the second detected wavelength band, that is, is configured so as to have the same function as that of the filter 232 of the first embodiment.

According to such a configuration, the color mixture image reflected by the dichroic mirror 48b passes through the fluorescence detection filter 231A, and thereby becomes an image having only the first detected wavelength band. The image pickup device 23c1 converts the image having only the first detected wavelength band to an image pickup signal and outputs the image pickup signal to the pre-processing section 42.

Furthermore, according to the aforementioned configuration, the color mixture image that has passed through the dichroic mirror 48b passes through the fluorescence detection filter 232A and becomes an image having only the second detected wavelength band. The image pickup device 23c2 converts the image having only the second detected wavelength band to an image pickup signal and outputs the image pickup signal to the pre-processing section 42.

Of the components provided in the image pickup section 61, suppose the dichroic mirrors 48a and 48b, the excitation light cut filter 49 and the fluorescence detection filters 231A and 232A have any one of cassette type and slot type configurations which facilitates replacement from outside of the processor 4A.

Next, the operation of the endoscope system 1A will be described. The operation and processing until the calculation results of the correction values α and β are stored in the memory 46 similar to those in the first embodiment are applicable in the endoscope system 1A. Thus, suppose the operation and processing of each section of the endoscope system 1A after storing the calculation results of the correction values α and β in the memory 46 will be mainly described below.

The user inserts the insertion portion 21 of the endoscope 2A into the body cavity of the examinee and installs the distal end portion 21a so that illumination light is emitted to the position where a desired object such as cancer exists.

Furthermore, the user scatters or injects the first and second fluorescent probes into the desired object such as cancer, using a treatment instrument (not shown) having a shape and size that allows it to be inserted into the endoscope 2A.

When the first and second fluorescent probes are scattered or injected into the desired object such as cancer, first fluorescent light having intensity corresponding to the amount of first biological protein which is the target of the first fluorescent probe and second fluorescent light having intensity corresponding to the amount of second biological protein which is the target of the second fluorescent probe are emitted simultaneously. An optical image corresponding to the returning light having the first fluorescent light and the second fluorescent light is impinged on the image pickup section 61 of the processor 4A via the image guide 25.

The dichroic mirror 48a reflects an RGB image out of the optical image outputted from the other end face (exit end face) of the image guide 25 toward the image pickup device 22c side and allows to pass the color mixture image other than the RGB image to the dichroic mirror 48b side.

The image pickup device 22c converts the RGB image reflected by the dichroic mirror 48a to an image pickup signal and outputs the image pickup signal to the pre-processing section 42.

Of the color mixture image that has passed through the excitation light cut filter 49, the dichroic mirror 48b reflects part thereof toward the fluorescence detection filter image pickup device 23c1 side and allows to pass the other part to the fluorescence detection filter image pickup device 23c2 side.

The image pickup device 23c1 converts an image having only the first detected wavelength band generated when the color mixture image reflected by the dichroic mirror 48b passes through the fluorescence detection filter 231A to an image pickup signal and outputs the image pickup signal to the pre-processing section 42. Furthermore, the image pickup device 23c2 converts an image having only the second detected wavelength band generated when the color mixture image passed through the dichroic mirror 48b passes through the fluorescence detection filter 232A to an image pickup signal and outputs the image pickup signal to the pre-processing section 42.

The first image pickup signal outputted from the image pickup device 22c is subjected to the aforementioned signal processing by the pre-processing section 42, stored in the frame memory section 43n and then a latest one-frame portion thereof is read by the normal light image generation section 44n. The normal light image generation section 44n generates a normal light image (full color image) corresponding to the image pickup signal and outputs the normal light image to the post-processing section 45 using the latest one-frame portion of the first image pickup signal stored in the frame memory section 43n.

On the other hand, a third image pickup signal outputted from the image pickup device 23c1 is subjected to the aforementioned signal processing by the pre-processing section 42, stored in the frame memory section 43f. Furthermore, a fourth image pickup signal outputted from the image pickup device 23c2 is subjected to the aforementioned signal processing by the pre-processing section 42 and stored in the frame memory section 43f.

In this case, the third image pickup signal outputted from the image pickup device 23c1 and the fourth image pickup signal outputted from the image pickup device 23c2 are stored in the frame memory section 43f in units of one frame respectively.

After that, the calculation section 47 simultaneously reads the latest one-frame portion of the third image pickup signal and the latest one-frame portion of the fourth image pickup signal from the frame memory section 43f. The calculation section 47 then generates a third fluorescence detected image based on the third image pickup signal and generates a fourth fluorescence detected image based on the fourth image pickup signal.

Here, the third fluorescence detected image is an image that can be used substantially in the same way as the first fluorescence detected image described in the first embodiment. Furthermore, the fourth fluorescence detected image is an image that can be used substantially in the same way as the second fluorescence detected image described in the first embodiment. Thus, assuming the luminance values corresponding to the same pixel in the third and fourth fluorescence detected images as P1 and P2 respectively, the values of the luminance values Pa and Pb can be obtained using above equations (1) and (2) in the same way as the method described in the first embodiment.

The calculation section 47 performs processing of replacing the luminance value P1 by the luminance value Pa for all pixels of the third fluorescence detected image, and thereby generates the aforementioned first fluorescent light image. Since the first fluorescent light image generated through such processing has only the luminance value corresponding to the intensity of the first fluorescent light emitted from the first fluorescent probe, the image becomes such an image where degradation of contrast caused by a crosstalk phenomenon is drastically reduced.

Furthermore, the calculation section 47 performs processing of replacing the luminance value P2 by the luminance value Pb for all pixels of the fourth fluorescence detected image, and thereby generates the aforementioned second fluorescent light image. Since the second fluorescent light image generated through such processing has only the luminance value corresponding to the intensity of the fluorescent light emitted from the second fluorescent probe, the image becomes such an image where degradation of contrast caused by a crosstalk phenomenon is drastically reduced.

After that, the calculation section 47 outputs the first and second fluorescent light images to the post-processing section 45.

The post-processing section 45 applies processing such as D/A conversion to the normal light image outputted from the normal light image generation section 44n and the first and second fluorescent light images outputted from the fluorescent light image generation section 44f and then outputs the images to the display section 5 as video signals.

As described above, the endoscope system 1A applies correction processing based on the fluorescence spectral waveform specific to each fluorescent probe to the detection results of a plurality of fluorescent light beams emitted from a plurality of fluorescent probes, and thereby has a configuration and operation that can acquire a fluorescent light image where degradation of contrast caused by a crosstalk phenomenon is drastically reduced. That is, the endoscope system 1A can stably reduce a crosstalk phenomenon generated when observing fluorescent light emitted from a plurality of fluorescent probes without depending on the concentration of each fluorescent probe, intensity of excitation light and an observation environment such as observation distance.

Furthermore, the endoscope system 1A rewrites information stored in the ID information storage section 24 of the endoscope 2A, changes the configuration of each section of the image pickup section 61 of the processor 4A to one corresponding to the information after the rewriting, and can thereby adopt a system configuration capable of supporting fluorescent probes other than the first and second fluorescent probes. That is, the endoscope system 1A can flexibly change the system configuration for combinations of various fluorescent light probes without changing the configuration of the endoscope 2A whenever possible.

Third Embodiment

Figure 10:
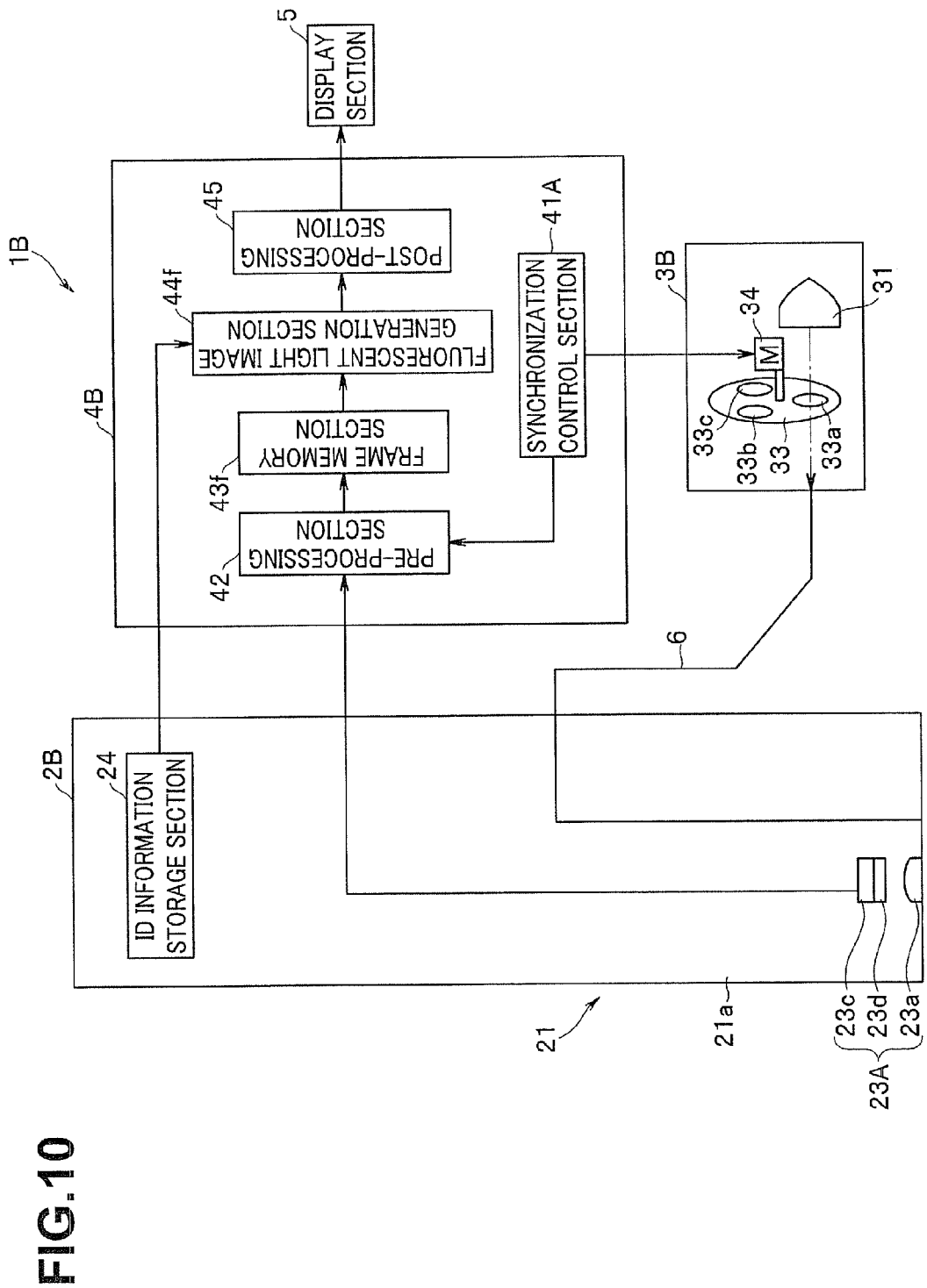
FIG. 10 is a diagram illustrating a configuration of main parts of an endoscope system according to a third embodiment of the present invention.

FIG. 10 is related to a third embodiment of the present invention.

In the following descriptions, detailed descriptions of components similar to those in the aforementioned embodiments will be omitted. Furthermore, the configuration of the endoscope system of the present embodiment has a configuration similar to that in the aforementioned embodiments. Thus, suppose parts different from those in the aforementioned embodiments will be mainly described in the present embodiment.

As shown in FIG. 10, an endoscope system 1B has an endoscope 2B that acquires an object image in the body cavity of an examinee and outputs an image pickup signal according to the object image, a light source apparatus 3B that sequentially supplies excitation light and reference light to the endoscope 2B, a processor 4B that converts the image pickup signal outputted from the endoscope 2B to a video signal and outputs the video signal and a display section 5 that displays the object image corresponding to the video signal outputted from the processor 4B on a screen.

A fluorescent light image pickup system 23A is provided at a distal end portion 21a of an insertion portion 21 of the endoscope 2B.

The fluorescent light image pickup system 23A provided with the function as a fluorescence detection section is configured by including an objective optical system 23a that forms an object image, an excitation light cut filter 23d disposed after the objective optical system 23a and an image pickup device 23c disposed after the excitation light cut filter 23d and at an image forming position of the objective optical system 23a.

The excitation light cut filter 23d is configured to cut off a wavelength band of excitation light supplied from the light source apparatus 3B and allow to pass bands other than the wavelength band of the excitation light.

An ID information storage section 24 of the endoscope 2B stores at least information on the wavelength band cut off by the excitation light cut filter 23d. The information is outputted to the processor 4B when the endoscope 2B and the processor 4B are electrically connected.

The light source apparatus 3B as a light source section is configured by including a lamp 31, a revolving filter 33 provided with a plurality of filters sequentially inserted in the optical path of the lamp 31 and a motor 34 that generates a drive force to rotate the revolving filter 33.

A diaphragm (not shown) for adjusting a light quantity of white color light emitted from the lamp 31 is provided between the lamp 31 and the revolving filter 33. The aforementioned diaphragm may be adjusted to an appropriate narrowing amount of diaphragm based on the brightness of a reference light image outputted from the calculation section 47 (fluorescent light image generation section 44f) of the processor 4 or may be adjusted to an appropriate narrowing amount of diaphragm corresponding to the user's operation.

The revolving filter 33 is configured into a disk shape, the center of which is the axis of rotation. Furthermore, the revolving filter 33 includes an excitation light filter 33a that allows to pass the excitation wavelength band of the first fluorescent probe, an excitation light filter 33b that allows to pass the excitation wavelength band of the second fluorescent probe and a reference light filter 33c that allows to pass a green color region, each provided along a circumferential direction on the outer circumferential side. According to such a configuration, the excitation light filter 33a, the excitation light filter 33b and the reference light filter 33c are sequentially inserted in the optical path of the lamp 31 and frame sequential light is supplied to the light guide 6. The present embodiment will be described assuming that the transmission wavelength band of the excitation light filter 33a is equal to the aforementioned first detected wavelength band and the transmission wavelength band of the excitation light filter 33b is equal to the aforementioned second detected wavelength band. Furthermore, suppose the excitation light cut filter 23d is configured to cut off the transmission wavelength band of the excitation light filter 33a and the transmission wavelength band of the excitation light filter 33b.

The transmittances of the excitation light filter 33a, the excitation light filter 33b and the reference light filter 33c may be adjusted beforehand so that the brightness of the reference light (of the returning light) received by the image pickup device 23c is optimally balanced with the brightness of the fluorescent light received by the image pickup device 23c after being emitted from the first and (or) second fluorescent light probes (so as to fall within the dynamic range of the image pickup device 23c). Furthermore, the transmittances of the excitation light filter 33a and the excitation light filter 33b may be adjusted beforehand so that the brightness of the fluorescent light received by the image pickup device 23c after being emitted from the first fluorescent light probe is optimally balanced with the brightness of the fluorescent light received by the image pickup device 23c after being emitted from the second fluorescent light probe (so as to fall within the dynamic range of the image pickup device 23c).

The processor 4B is configured by including a synchronization control section 41A, a pre-processing section 42, a frame memory section 43f, a fluorescent light image generation section 44f and a post-processing section 45.

The synchronization control section 41A performs control for synchronizing the rotation speed of the motor 34 with timing at which an image pickup signal is outputted from the pre-processing section 42 to the frame memory section 43f as appropriate.

A memory 46 of the processor 4B stores absorption spectral waveforms of a plurality of fluorescent probes. The present embodiment will be described assuming that the absorption spectral waveform of the first fluorescent probe is equal to the aforementioned fluorescence spectral waveform and the absorption spectral waveform of the second fluorescent probe is equal to the aforementioned fluorescence spectral waveform.

Furthermore, the ID information storage section 24 of the endoscope 2B may be provided in the light source apparatus 3B as one that stores at least the information on the transmission wavelength bands of the excitation light filters 33a and 33b and may output the information to the processor 4B when the endoscope 2B and the light source apparatus 3B are electrically connected.

Next, the operation of the endoscope system 1B will be described.

First, after connecting each section of the endoscope system 1B, the user turns on power of the each section. Accordingly, when the endoscope 2B and the processor 4B are electrically connected, a calculation section 47 reads the information on the wavelength band cut off by the excitation light cut filter 23d from the ID information storage section 24. Furthermore, the calculation section 47 reads the absorption spectral waveform of the fluorescent probe corresponding to the information from the memory 46.

Here, in view of the fact that the absorption spectral waveforms of the first and second fluorescent probes overlap with each other in the diagonally shaded area in FIG. 6 and the absorption spectral waveforms of the first and second fluorescent probes and the transmission wavelength bands (wavelength λda1 to λda2) of the excitation light filter 33a and the transmission wavelength bands (wavelength λdb1 to λdb2) of the excitation light filter 33b have a relationship as shown in FIG. 6, the correction values α and β can be calculated using a method similar to the method described in the first embodiment. The calculation section 47 causes the memory 46 to temporarily store the calculation results of the correction values α and β, obtained through the calculation processing using a method similar to the method described in the first embodiment.

On the other hand, the user inserts the insertion portion 21 of the endoscope 2B into the body cavity of an examinee and installs the distal end portion 21α so that illumination light is emitted to the position where a desired object such as cancer exists. Thus, two types of excitation light and the reference light are sequentially emitted to the desired object.

The user then scatters or injects the first and second fluorescent probes into the desired object such as cancer, using a treatment instrument (not shown) having a shape and size that allows it to be inserted into the endoscope 2B.

When the first and second fluorescent probes are scattered or injected into the desired object such as cancer, first fluorescent light having intensity corresponding to the amount of first biological protein which is the target of the first fluorescent probe and second fluorescent light having intensity corresponding to the amount of second biological protein which is the target of the second fluorescent probe are emitted respectively. Returning light having the first fluorescent light and the second fluorescent light is impinged on the objective optical system 23a.

Furthermore, when the returning light impinged on the objective optical system 23a passes through the excitation light cut filter 23d, images of the first fluorescent light, the second fluorescent light and the reference light are sequentially formed by the image pickup device 23c. The image pickup device 23c then converts the object images corresponding to the first fluorescent light, the second fluorescent light and the reference light to image pickup signals respectively and sequentially outputs the image pickup signals to the processor 4B.

The pre-processing section 42 applies the aforementioned signal processing to the three types of image pickup signals sequentially outputted from the image pickup device 23c and then simultaneously outputs the three types of image pickup signals to the frame memory section 43f in units of one frame at timings corresponding to the control of the synchronization control section 41A.

In this case, the image pickup signal corresponding to the first fluorescent light, the image pickup signal corresponding to the second fluorescent light and the image pickup signal corresponding to the reference light are stored in the frame memory section 43f in units of one frame respectively.

After that, the calculation section 47 simultaneously reads the latest one-frame portion of the image pickup signal corresponding to the first fluorescent light, the latest one-frame portion of the image pickup signal corresponding to the second fluorescent light and the latest one-frame portion of the image pickup signal corresponding to the reference light from the frame memory section 43f. The calculation section 47 then generates a fifth fluorescence detected image based on the image pickup signal corresponding to the first fluorescent light, generates a sixth fluorescence detected image based on the image pickup signal corresponding to the second fluorescent light and generates a reference light image based on the image pickup signal corresponding to the reference light.

Here, the fifth fluorescence detected image is an image that can be used substantially in the same way as for the first fluorescence detected image described in the first embodiment. Furthermore, the sixth fluorescence detected image is an image that can be used substantially in the same way as for the second fluorescence detected image described in the first embodiment. Therefore, assuming the luminance values corresponding to the same pixel of the fifth and sixth fluorescence detected images are P1 and P2, the luminance values Pa and Pb can be obtained using equations (1) and (2) above in the same way as in the method described in the first embodiment.

The calculation section 47 performs processing of replacing the luminance value P1 by the luminance value Pa for all pixels of the fifth fluorescence detected image, and thereby generates the aforementioned first fluorescent light image. The first fluorescent light image generated through such processing has only the luminance value according to the intensity of the fluorescent light emitted from the first fluorescent probe and becomes an image where degradation of contrast caused by a crosstalk phenomenon is drastically reduced.

Furthermore, the calculation section 47 performs processing of replacing the luminance value P2 by the luminance value Pb for all pixels of the sixth fluorescence detected image, and thereby generates the aforementioned second fluorescent light image. The second fluorescent light image generated through such processing has only the luminance value according to the intensity of the fluorescent light emitted from the second fluorescent probe and becomes an image where degradation of contrast caused by a crosstalk phenomenon is drastically reduced.

After that, the calculation section 47 outputs the first and second fluorescent light images and the reference light image to the post-processing section 45.

The post-processing section 45 of the processor 4B applies processing such as coloration in pseudo-colors and D/A conversion to the first and second fluorescent light images outputted from the fluorescent light image generation section 44f and the reference light image and outputs the images to the display section 5 as video signals.

When generating video signals, the post-processing section 45 of the processor 4B may perform processing of simultaneously displaying the first fluorescent light image, the second fluorescent light image and the reference light image on one screen or processing of displaying only images according to an instruction given by a display mode changeover switch (not shown).

Furthermore, when generating video signals, the post-processing section 45 may perform processing of displaying any one of the first fluorescent light image and the second fluorescent light image superimposed on the reference light image.

Furthermore, the present embodiment may perform processing of coloring the first fluorescent light image and the second fluorescent light image in different colors and displaying the colored fluorescent light images superimposed on a separately acquired normal light image.

As described above, by applying correction processing based on absorption spectral waveforms specific to each fluorescent probe to the detection results of a plurality of fluorescent light beams emitted from a plurality of the fluorescent probes, the endoscope system 1B has a configuration and operation capable of acquiring a fluorescent light image where degradation of contrast caused by a crosstalk phenomenon is drastically reduced. That is, the endoscope system 1B can stably reduce a crosstalk phenomenon generated when observing fluorescent light emitted from a plurality of fluorescent probes without depending on the concentration of each fluorescent probe, intensity of excitation light and an observation environment such as observation distance.

The configuration of the endoscope system 1B of the present embodiment can also reduce a crosstalk phenomenon generated when observing autofluorescent light beams emitted from a plurality of autofluorescent substances in the living body. To be more specific, the configuration of the endoscope system 1B of the present embodiment is also applicable for the purpose of acquiring autofluorescent light images of the mucous membrane of the alimentary tract separated for each layer.

When the endoscope system 1B is applied for the aforementioned purpose, the excitation light filter 33a of the light source apparatus 3B is configured so as to allow to pass the wavelength band capable of exciting a first autofluorescent substance which exists in the living tissue. Furthermore, when the endoscope system 1B is applied for the aforementioned purpose, the excitation light filter 33b of the light source apparatus 3B is configured so as to allow to pass the wavelength band capable of exciting a second autofluorescent substance which exists in the living tissue. Accordingly, the excitation light cut filter 23d is configured so as to cut off the wavelength bands of the excitation light beams generated by the excitation light filters 33a and 33b.

Furthermore, when the endoscope system 1B is applied for the aforementioned purpose, the user prepares a sample of a cross section of living tissue containing the aforementioned first and second autofluorescent substances and substantially matching the mucous membrane structure of the alimentary tract, before their actual observation of the living body. After that, the user irradiates a plurality of excitation light beams having different wavelength bands onto the sample individually and picks up images of the sample using the endoscope 2B every time each excitation light beam is irradiated, and thereby acquires a plurality of spectral images. Suppose the plurality of excitation light beams include at least light of the wavelength band for exciting the first autofluorescent substance and light of the wavelength band for exciting the second autofluorescent substance.

The plurality of spectral images obtained as described above are stored beforehand in the memory 46 associated in a one-to-one correspondence with the wavelength bands of the excitation light beams used to acquire the spectral images.

Here, the operation when the endoscope system 1B is applied for the aforementioned purpose will be described.

First, the user connects each section of the endoscope system 1B and then turns on power of the each section. Accordingly, the calculation section 47 reads, when the endoscope 2B and the processor 4B are electrically connected, information on the wavelength band cut off by the excitation light cut filter 23d from the ID information storage section 24.

After that, the calculation section 47 reads a spectral image corresponding to the information from the memory 46. To be more specific, the calculation section 47 reads a first spectral image picked up when light of the wavelength band corresponding to the transmission wavelength band of the excitation light filter 33a is irradiated onto the aforementioned sample and a second spectral image picked up when light of the wavelength band corresponding to the transmission wavelength band of the excitation light filter 33b is irradiated onto the aforementioned sample from the memory 46.

On the other hand, the calculation section 47 provided with the function as a correction value calculation section reads the first and second spectral images from the memory 46 and then calculates average luminance×1 of the mucous membrane layer in the first spectral image and average luminance×2 of the mucous membrane layer in the second spectral image. The calculation section 47 then calculates a correction value s by subtracting the value of average luminance×2 from the value of average luminance×1.

Furthermore, the calculation section 47 provided with the function as a correction value calculation section reads the first and second spectral images from the memory 46 and then calculates average luminance Y1 of the submucosa in the first spectral image and average luminance Y2 of the submucosa in the second spectral image. The calculation section 47 then calculates a correction value t by subtracting the value of the average luminance Y2 from the value of the average luminance Y1.

After that, the calculation section 47 causes the memory 46 to store the calculated correction values s and t.

Next, the user inserts the insertion portion 21 of the endoscope 2B into the body cavity of the examinee and installs the distal end portion 21α at a position facing the surface of the mucous membrane of the alimentary tract in the body cavity. Thus, two types of excitation light and reference light are sequentially emitted to the mucous membrane of the alimentary tract.

When the excitation light generated by the excitation light filters 33a and 33b is emitted to the mucous membrane of the alimentary tract, first autofluorescent light corresponding to the first autofluorescent substance and second autofluorescent light corresponding to the second autofluorescent substance are emitted respectively. Returning light provided with the first and second autofluorescent light beams is impinged on the objective optical system 23a.

Furthermore, when the returning light impinged on the objective optical system 23a passes through the excitation light cut filter 23d, images of the first autofluorescent light, the second autofluorescent light and the reference light are sequentially formed on the image pickup device 23c. The image pickup device 23c then converts object images corresponding to the first autofluorescent light, the second autofluorescent light and the reference light to image pickup signals and sequentially outputs the image pickup signals to the processor 4B.

The pre-processing section 42 applies the aforementioned signal processing to three types of image pickup signals sequentially outputted from the image pickup device 23c and then simultaneously outputs the three types of image pickup signals to the frame memory section 43f in units of one frame at timings according to the control of the synchronization control section 41A.

In this case, the frame memory section 43f stores the image pickup signal corresponding to the first autofluorescent light, the image pickup signal corresponding to the second autofluorescent light and the image pickup signal corresponding to the reference light in units of one frame respectively.

After that, the calculation section 47 simultaneously reads the latest one-frame portion of the image pickup signal corresponding to the first autofluorescent light, the latest one-frame portion of the image pickup signal corresponding to the second autofluorescent light and the latest one-frame portion of the image pickup signal corresponding to the reference light from the frame memory section 43f respectively. The calculation section 47 provided with the function as a detected image generation section generates a first autofluorescence detected image based on the image pickup signal corresponding to the first autofluorescent light, generates a second autofluorescence detected image based on the image pickup signal corresponding to the second autofluorescent light and generates a reference light image based on the image pickup signal corresponding to the reference light.

Now, the aforementioned first and second autofluorescence detected images are a mixture of the autofluorescent light image of the mucous membrane layer and the autofluorescent light image of the submucosa. Here, assuming that luminance values corresponding to the same pixel in the first and second autofluorescence detected images are T1 and T2 respectively, a luminance value of the autofluorescent light image of the mucous membrane layer is Tm and a luminance value of the autofluorescent light image of the submucosa is Tsm, a relationship shown in following equations (3) and (4) holds between each value and correction values s and t.

$$Tm = T1 - tT2 \qquad (3)$$

$$Tsm = T1 - sT2 \qquad (4)$$

After reading the calculation results of the correction values s and t from the memory 46, the calculation section 47 calculates luminance values Tm and Tsm for all pixels of the first and second spectral images using equations (3) and (4) above.

Furthermore, the calculation section 47 performs processing of replacing the luminance value T1 by the luminance value Tm for all pixels of the first autofluorescence detected images, and thereby generates an autofluorescent light image of the mucous membrane layer. Furthermore, the calculation section 47 performs processing of replacing the luminance value T2 by the luminance value Tsm for all pixels of the second autofluorescence detected images, and thereby generates an autofluorescent light image of the submucosa. Through such processing, the autofluorescent light image of the mucous membrane layer and the autofluorescent light image of the submucosa can be obtained separately (individually).

After that, the calculation section 47 outputs the autofluorescent light image of the mucous membrane layer, the autofluorescent light image of the submucosa and the reference light image to the post-processing section 45.

The post-processing section 45 of the processor 4B applies processing such as coloration in pseudo-colors and D/A conversion to the autofluorescent light image of the mucous membrane layer, the autofluorescent light image of the submucosa outputted from the fluorescent light image generation section 44f and the reference light image and then outputs the images to the display section 5 as video signals.

When generating video signals, the post-processing section 45 of the processor 4B may also perform processing of simultaneously displaying the autofluorescent light image of the mucous membrane layer, the autofluorescent light image of the submucosa and the reference light image on one screen or processing of displaying only images according to an instruction given by a display mode changeover switch (not shown).

Furthermore, when generating video signals, the post-processing section 45 may perform processing of displaying any one of the autofluorescent light image of the mucous membrane layer and the autofluorescent light image of the submucosa, superimposed on the reference light image.

It goes without saying that the present invention is not limited to the aforementioned embodiments but can be modified in various ways without departing from the spirit and scope of the invention.

What is claimed is:

1. A fluorescence observation apparatus comprising:
   a light source section that emits excitation light for exciting a first fluorescent substance and a second fluorescent substance;
   a fluorescence detection section that detects first fluorescent light emitted when the first fluorescent substance is excited by the excitation light and second fluorescent light emitted when the second fluorescent substance is excited by the excitation light;
   a correction value calculation section that calculates a correction value for canceling a color mixture between the first fluorescent light and the second fluorescent light based on feature values corresponding to characteristics of the first fluorescent substance and the second fluorescent substance;
   a detected image generation section that generates a first detected image corresponding to a detection result of the first fluorescent light in the fluorescence detection section and a second detected image corresponding to a detection result of the second fluorescent light in the fluorescence detection section; and
   an image correction section that corrects a luminance value of each pixel of the first detected image to a luminance value corresponding to intensity of the first fluorescent light and corrects a luminance value of each pixel of the second detected image to a luminance value corresponding to intensity of the second fluorescent light based on the correction value.

2. The fluorescence observation apparatus according to claim 1, wherein the feature values comprise a fluorescence spectral waveform of the first fluorescent substance, a fluorescence spectral waveform of the second fluorescent substance, a first detected wavelength band used to detect the first fluorescent light and a second detected wavelength band used to detect the second fluorescent light.

3. The fluorescence observation apparatus according to claim 2, wherein the first detected wavelength band and the second detected wavelength do not overlap with each other.

4. The fluorescence observation apparatus according to claim 1, wherein the light source section simultaneously emits first excitation light for exciting the first fluorescent substance and second excitation light for exciting the second fluorescent substance.

5. The fluorescence observation apparatus according to claim 1, wherein the feature values comprise an absorption spectral waveform of the first fluorescent substance and an absorption spectral waveform of the second fluorescent substance.

6. The fluorescence observation apparatus according to claim 1, wherein the light source section sequentially emits first excitation light for exciting the first fluorescent substance and second excitation light for exciting the second fluorescent substance.

7. A fluorescence observation apparatus comprising:
   a light source section that emits excitation light to an object to be examined having a first fluorescent substance and a second fluorescent substance;
   a fluorescence detection section that detects first fluorescent light emitted when the first fluorescent substance is excited by the excitation light and second fluorescent light emitted when the second fluorescent substance is excited by the excitation light;
   a correction value calculation section that calculates a correction value based on a first spectral image obtained by picking up an image of the object to be examined formed by light of a wavelength band that excites the first fluorescent substance and a second spectral image obtained by picking up an image of the object to be examined formed by light of a wavelength band that excites the second fluorescent substance;
   a detected image generation section that generates a first detected image corresponding to a detection result of the first fluorescent light in the fluorescence detection section and a second detected image corresponding to a detection result of the second fluorescent light in the fluorescence detection section; and
   an image correction section that corrects a luminance value of each pixel of the first detected image to a luminance value corresponding to intensity of the first fluorescent light and corrects a luminance value of each pixel of the second detected image to a luminance value corresponding to intensity of the second fluorescent light based on the correction values.

8. The fluorescence observation apparatus according to claim 7, wherein the correction value corresponds to a ratio of the luminance value of the first spectral image to the luminance value of the second spectral image.

9. The fluorescence observation apparatus according to claim 7, wherein the light source section sequentially emits first excitation light for exciting the first fluorescent substance and second excitation light for exciting the second fluorescent substance.

* * * * *